United States Patent [19]

Szarka et al.

[11] 4,208,481
[45] Jun. 17, 1980

[54] USE OF PHENYLALKANES AS PRECURSORS IN BENZYLPENICILLIN FERMENTATION

[75] Inventors: Laszlo J. Szarka, East Brunswick; Robert W. Eltz, Princeton, both of N.J.

[73] Assignee: E. R. Squibb & Sons, Inc., Princeton, N.J.

[21] Appl. No.: 961,306

[22] Filed: Nov. 16, 1978

[51] Int. Cl.$^2$ ............................................. C12P 37/00
[52] U.S. Cl. ........................................ 435/43; 435/46
[58] Field of Search .................... 195/36 P; 435/43, 46

[56] References Cited

U.S. PATENT DOCUMENTS

| 2,423,873 | 7/1947 | Coghill et al. | 195/36 P |
|---|---|---|---|
| 2,451,853 | 10/1948 | Mead et al. | 195/36 P |
| 2,641,567 | 6/1953 | Perlman et al. | 195/36 P |
| 3,301,766 | 1/1967 | Douros et al. | 195/28 R |

FOREIGN PATENT DOCUMENTS

28432 of 1974 Japan.

OTHER PUBLICATIONS

Singh et al., J. Bact., vol. 56, pp. 339-355 (1948).
Behrens et al., J. Biological Chem., vol. 175, pp. 751-764 (1948).
Tabenkin et al., Archieves of Biochemistry and Biophysics, vol. 38, pp. 43-48 (1952).
Science, vol. 106, pp. 503-505 (1947).
Umezawa et al., Chem. Abst., vol. 43, p. 3060f (1947).
Demain, Biosynthesis of Antibiotics, vol. 1, pp. 30-42 (1966).

Perlman, Annals New York Academy of Sciences, vol. 139, pp. 258-269 (1966).
Pidoplichko et al., Chem. Abst., vol. 71, p. 46903r (1969).
The American Type Culture Collection, Catalogue of Strains, 10th Edition, p. 164 (1972).
Avanzini et al., Annals New York Academy of Sciences, vol. 153, pp. 534-540 (1968).
Niedermayer, Analytical Chemistry, vol. 36, pp. 938-939 (1964).
Webley et al., Nature, vol. 178, pp. 1467-1468 (1956).
Davis et al., Applied Microbiology, vol. 9, pp. 383-388 (1961).
Davis, Petroleum Microbiology, pp. 327-331 (1967).
Douros et al., Applied Microbiology, vol. 16, pp. 320-325, 532-533 (1968).

*Primary Examiner*—Alvin E. Tanenholtz
*Attorney, Agent, or Firm*—Lawrence S. Levinson; Stephen B. Davis

[57] ABSTRACT

Benzylpenicillin is prepared by culturing a penicillin-producing microorganism in a medium containing suitable sources of nitrogen, carbon and energy, and inorganic salts. One or more phenylalkanes of the formula

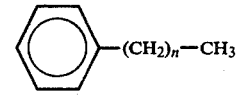

wherein n is an integer from 6 to 13 are included within the medium as the sidechain precursor.

9 Claims, No Drawings

USE OF PHENYLALKANES AS PRECURSORS IN BENZYLPENICILLIN FERMENTATION

BACKGROUND OF THE INVENTION

Benzylpenicillin, i.e. 3,3-dimethyl-7-oxo-6-[(phenylacetyl)amino]-4-thia-1-azabicyclo[3.2.0]heptane-2-carboxylic acid commonly referred to as penicillin G, is a widely prescribed antibacterial agent. Benzylpenicillin is available in the free acid, salt, and ester forms and is formulated for oral or parenteral use.

Benzylpenicillin is conventionally prepared by fermentation. A penicillin-producing microorganism is cultured in a medium containing a source of nitrogen, a source of carbon and energy, various inorganic salts, and a sidechain precursor. It has been known since the 1940 s that in order to obtain relatively pure benzylpenicillin in suitable yields as the fermentation product rather than a mixture of penicillins, a sidechain precursor should be present in the medium.

Phenylacetic acid and its salts such as potassium phenylacetic acid are conventionally employed as benzylpenicillin sidechain precursors. Other benzylpenicillin precursors disclosed by Singh et al, J. Bact. Vol. 56, p. 339-355 (1948), include octadecanol phenylacetate, phenylacetamide, phenylacetyl-D,L-alanine, phenylacetylglycine, $\beta$-phenylethylamine, and D,L-phenylalanine. Various phenylacetic acid derivatives are taught as benzylpenicillin precursors by Behrens et al, Journal of Biological Chem., Vol. 175, p. 751-764, Tabenkin et al, Archives of Biochemistry and Biophysics, Vol. 38, p. 43-48, and the Editorial Board of the Monograph on the Chemistry of Penicillins, Science, Vol. 106, p. 503-505. Substituted phenylacetic acids are also disclosed as benzylpenicillin precursors by Umezawa et al, Chem. Abst., Vol. 43, p. 3060f and N-(2-hydroxyethyl)phenylacetamide is disclosed by Perlman et al in U.S. Pat. No. 2,641,567.

Nara et al in Japanese Patent 28432 (1974) disclose producing benzylpenicillin or Penicillin V in a fermentation medium containing n-paraffins as the carbon source and phenylacetic acid or phenoxyacetic acid as the sidechain precursor.

Similarly, Pidoplichko et al, Chem. Abst., Vol. 71, p. 46903r, disclose that Penicillium species are able to use hydrocarbons, hexadecane, higher secondary alcohols, $C_{17-20}$ fatty acids, and higher paraffins as the sole source of carbon.

SUMMARY OF THE INVENTION

This invention is directed to the fermentative production of benzylpenicillin. A penicillin-producing microorganism is cultured in a medium containing suitable sources of nitrogen, carbon and energy, and inorganic salts. The medium also includes as the sidechain precursor one or more phenylalkanes of the formula

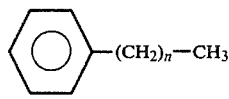

wherein n is an integer from 6 to 13.

DETAILED DESCRIPTION

This invention is directed to producing benzylpenicillin by a conventional fermentative biosynthetic process except that one or more phenylalkanes of the formula

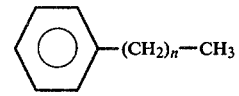

wherein n is an integer from 6 to 13 is included within the fermentation medium as the sidechain precursor.

By the term "conventional fermentation process" it is meant that the process conditions, the penicillin-producing microorganism, the nitrogen source, the carbon and energy source, and the salts present within the culture medium are those commonly employed in the production of benzylpenicillin.

Suitable nitrogen sources for inclusion within the culture medium include various inorganic or organic salts or compounds such as urea, liquid ammonia, or ammonium salts such as ammonium chloride, ammonium sulfate, ammonium nitrate, ammonium acetate, ammonium phosphate, etc., and mixtures thereof. Corn-steep liquor, which is a mixture of various nitrogen sources and inorganic compounds, is a preferred component of the culture medium.

Suitable carbon and energy sources for inclusion within the culture medium include carbohydrates such as lactose, glucose, sucrose, etc., and mixtures thereof. Other materials which can be employed include ethanol and various n-paraffins. A fatty oil such as lard oil, peanut oil, corn oil, etc., can also be included within the culture medium as taught by Perlman in U.S. Pat. No. 2,641,567.

Suitable inorganic salts for inclusion within the culture medium include magnesium sulfate, sodium phosphate, sodium nitrate, potassium monohydrogen phosphate, potassium dihydrogen phosphate, iron sulfate, manganese chloride, calcium chloride, calcium carbonate, sodium chloride, zinc sulfate, etc., and mixtures thereof.

Culturing is conducted under aerobic conditions, such as aerobic shaking of the culture or aeration of a submerged culture with agitation. The temperature employed can vary from about 20° C. to about 28° C. and the pH can be from about 5.0 to about 7.5. Culturing is generally carried out for from about 5 to about 10 days. The resulting benzylpenicillin is separated from the culture medium by conventional techniques such as extraction and crystallization procedures.

This process can employ various penicillin producing cultures. In general those of the Penicillium type are preferred, with *Penicillium chrysogenum* being most preferred.

The phenylalkane sidechain precursors can be employed in this process in a similar manner to the phenylacetic acid salts. Thus, the phenylalkane or mixture of phenylalkanes can be added periodically in small amounts to the culture medium during the course of the fermentation process.

Preferably, the phenylalkanes employed in this process are one or more wherein n is an integer from 7 to 11. Most preferred are those wherein n is 8, 9 or 11. These most preferred phenylalkanes are less toxic to the penicillin-producing microorganisms than the commercially employed potassium phenylacetic acid. Consequently, these most preferred phenylalkanes can be added in toto to the initial culture medium, thus eliminating the need for careful monitoring of the medium and the periodic introduction of additional sidechain precursor.

The following examples are illustrative of the invention.

EXAMPLES 1-4

The following examples demonstrate benzylpenicillin production achieved in fermentations employing various phenylalkane sidechain precursors as compared with a control (no sidechain precursor) fermentation. All of these fermentations employed the following culture medium:

|  | gram/liter in water |
| --- | --- |
| Lactose | 90 |
| Cornsteep liquor | 60 |
| $(NH_4)_2SO_4$ | 5 |
| $NaNO_3$ | 2 |
| $CaCO_3$ | 6 |
| $NaH_2PO_4$ | 4 |
| Lard Oil | 3 |
| $MgSO_4 . 7H_2O$ | 0.25 |
| $MnSO_4 . 4H_2O$ | 0.025 |
| $ZnSO_4 . 7H_2O$ | 0.025 |
| $FeSO_4 . 7H_2O$ | 0.02 |

The penicillin-producing microorganism employed in these fermentations is *Penicillium chrysogenum* ATCC 12690 which is a known penicillin-producing culture publically available from the American Type Culture Collection, Rockville, Maryland.

The fermentations are performed as follows. 25.2 Liters of the above culture medium is sterilized in a 38 liter capacity fermentor. The fermentor is a stainless steel tank with a 300 mm. inner diameter equipped with three six-bladed turbo impellers. The tank is operated at 25° C. with sterile air supply at 3 vol./vol./min. The agitator speed is 680 rpm. The fermentor is inoculated with 2.8 liters of a thiry-hour-old broth culture of *Penicillium chrysogenum* ATCC 12690. The pH of the broth is controlled between 5.5 and 7.1 using 50% NaOH solution. The volume of each batch is adjusted to 28 to 30 liters with sterile water every 24 hours.

In Examples 1 to 4, 280 g. of the phenylalkane sidechain precursor is added to the fermentor initially. In the control no sidechain precursor is added.

The fermentations are performed for a given length of time after which the penicillin potency is determined in the broth by the hydroxylamine method. (Avanzini et al., Ann. N.Y. Acad. Sci., Vol. 153, p. 534-540.) The phenylacetic acid concentration in the broth is also determined. (Neidermayer, Anal. Chem., Vol. 36, p. 938-939.)

The presence of benzylpenicillin (Pen G) in the fermentation broth is confirmed by different methods. The first method comprises measuring the difference in free phenylacetic acid before and after enzymatically hydrolyzing the product to give phenylacetic acid and 6-APA. The amounts of phenylacetic acid are determined by gas chromatography as described above by Neidermayer. The following procedure is employed. 200 ml. of fermentation broth is centrifuged. A small amount of the supernatant fluid is removed and treated as set forth above to determine the amount of phenylacetic acid. The pH of 100 ml. of remaining supernatant fluid is adjusted to 8.0 by the addition of 0.1N NaOH solution. The temperature of the supernatant fluid is increased to 37° C. and 5 ml. of penicillin acylase preparation (derived from *Bacillus megaterium*) is added. Then the temperature and the pH are maintained at 37° and 8, respectively, for two hours. After this, 2 ml. of the mixture is adjusted to pH 1.8 with 60% (w/v) $H_2SO_4$ and extracted with 2 ml. of toluene. The toluene phase is analyzed for phenylacetic acid in a gas chromatographic system.

The presence of benzylpenicillin in the fermentation broth is also confirmed by a bioautogram technique. In this procedure, a sample of the fermentation broth is spotted on chromatography paper along with two standard samples which contain known amounts of benzylpenicillin and Pen K. The spots are developed and plated on an agar bioautographic plate which has been treated with *Staph. aureus*. The plate is incubated overnight. The zones of inhibition are measured and compared with the standards. By this procedure, the presence of benzylpenicillin in the fermentation broth is confirmed and the percentage of other penicillins within the broth can be determined.

The data obtained are summarized in the following table.

| Example | 1 | 2 | 3 | 4 | Control |
| --- | --- | --- | --- | --- | --- |
| Precursor | —$(CH_2)_9$—$CH_3$ | —$(CH_2)_7$—$CH_3$ | —$(CH_2)_8$—$CH_3$ | —$(CH_2)_{13}$—$CH_3$ | none |
| Length of Fermentation | 118 hours | 120 hours | 120 hours | 167 hours | 118 hours |
| Penicillin Potency (expressed as Pen G units/ml.) | 1704 | 1106 | 1382 | 1388 | 936 |
| Total Penicillin (expressed as billion units of Pen G) | 0.047 | 0.039 | 0.044 | 0.042 | 0.023 |
| Phenylacetic Acid before enzymatic hydrolysis (mg./ml.) | 0 | 0 | 0 | 0 | 0 |
| Total Phenylacetic Acid After Hydrolysis (gram) | 12.7 | 7.84 | 9.15 | 6.6 | 0 |
| Percentage of Pen G to total penicillins | ~100% | 87.8% | 90.8% | 68.6% | <30% |

What is claimed is:

1. The fermentative method of producing benzylpenicillin which comprises aerobically culturing a penicillin-producing microorganism in a medium containing a source of nitrogen, a source of carbon and energy, inorganic salts, and as the sidechain precursor one or more phenylalkanes of the formula

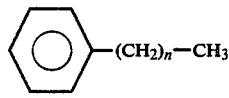

wherein n is an integer from 6 to 13, said fermentation process being performed without the addition of phenylacetic acid or its salts to the medium, followed by the step of recovering the benzylpenicillin from the medium.

2. The method of claim 1 wherein the penicillin-producing microorganism is of the Penicillium genus.

3. The method of claim 2 wherein the medium is at a temperature of from about 20° C. to about 28° C., the pH is at from about 5 to about 7.5, and the culturing is carried out for from about 5 to about 10 days.

4. The method of claim 3 wherein the sidechain precursor is one or more phenylalkanes of the formula

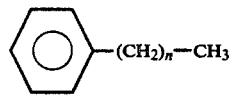

wherein n is an integer from 7 to 11.

5. The method of claim 4 wherein the sidechain precursor is one or more phenylalkanes of the formula

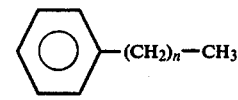

wherein n is 8, 9, or 11.

6. The method of claim 5 wherein the penicillin-producing microorganism is a strain of *Pencillium chrysogenum*.

7. The method of claim 6 wherein the sidechain precursor is

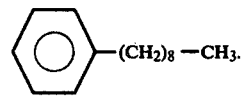

8. The method of claim 6 wherein the sidechain precursor is

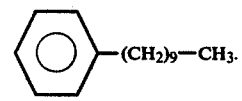

9. The method of claim 6 wherein the sidechain precursor is

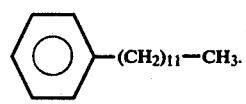

* * * * *